United States Patent
Coenen et al.

(10) Patent No.: US 6,652,686 B1
(45) Date of Patent: Nov. 25, 2003

(54) PROCESSES AND APPARATUS FOR MAKING DISPOSABLE ABSORBENT ARTICLES

(75) Inventors: Joseph Daniel Coenen, Neenah, WI (US); Robert Griffiths Brandon, Appleton, WI (US); Louis Maurice Chapdelaine, Appleton, WI (US); Scott Lee Kastman, Kansas City, MO (US); Robert Lee Popp, Hortonville, WI (US); Devertt DeWayne Woolwine, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/489,074

(22) Filed: Jan. 21, 2000

Related U.S. Application Data

(60) Provisional application No. 60/118,988, filed on Feb. 8, 1999.

(51) Int. Cl.⁷ .......................... B65H 23/00; B65H 20/00
(52) U.S. Cl. ......................... 156/64; 156/164; 156/351; 156/356; 156/357; 156/379; 226/2; 226/4
(58) Field of Search ........................ 156/64, 351, 367, 156/379, 356, 357, 229, 164, 259; 226/2, 4, 45

(56) References Cited

U.S. PATENT DOCUMENTS

| | | | |
|---|---|---|---|
| 2,682,909 A | 7/1954 | Claff et al. .................. 154/1.7 |
| 2,990,173 A | 6/1961 | Melville ....................... 270/52 |
| 3,004,880 A | 10/1961 | Lord ............................. 156/64 |
| 3,127,292 A | 3/1964 | Early ............................ 156/64 |
| 3,276,183 A | 10/1966 | Carlisle, Jr. et al. ............ 53/51 |
| 3,294,301 A | 12/1966 | Richter ......................... 226/27 |
| 3,326,436 A | 6/1967 | Huck ............................ 226/25 |
| 3,559,568 A | 2/1971 | Stanley ........................ 101/32 |
| 3,589,095 A | 6/1971 | James et al. ................... 53/51 |
| 3,762,125 A | 10/1973 | Prena ............................ 53/51 |
| 3,806,390 A | 4/1974 | Balk et al. ................... 156/229 |
| 3,811,987 A | 5/1974 | Wilkinson et al. .......... 156/497 |
| 3,887,419 A | 6/1975 | Geschwender .............. 156/197 |
| 3,978,637 A | 9/1976 | Mauriello ....................... 53/28 |
| 4,007,866 A | 2/1977 | Traise .......................... 226/31 |
| 4,018,028 A | 4/1977 | Donnet .......................... 53/51 |
| 4,070,226 A | 1/1978 | Crathern et al. ............. 156/364 |
| 4,129,238 A | 12/1978 | Herd ............................ 226/29 |
| 4,135,664 A | 1/1979 | Resh ........................... 235/475 |
| 4,239,570 A | 12/1980 | Kerwin ....................... 156/163 |
| 4,248,655 A | 2/1981 | Kerwin ....................... 156/351 |
| 4,254,173 A | 3/1981 | Peer, Jr. ..................... 428/204 |
| 4,295,912 A | 10/1981 | Burns ......................... 156/324 |

(List continued on next page.)

FOREIGN PATENT DOCUMENTS

| | | | |
|---|---|---|---|
| CA | 1 158 537 | 12/1983 | ........... B65B/41/18 |
| CA | 1 163 548 | 3/1984 | ........... B65B/41/18 |
| CA | 1253062 | 4/1989 | ........... B32B/31/08 |

(List continued on next page.)

*Primary Examiner*—Curtis Mayes
*Assistant Examiner*—Sue A. Purvis
(74) *Attorney, Agent, or Firm*—Pauley Petersen & Erickson

(57) ABSTRACT

A process and apparatus for registering a plurality of discrete components to a continuously moving first layer of material produces a disposable absorbent garment with improved alignment of the components on the first layer of material. The first layer has a plurality of reference marks positioned thereon. Various devices are used to compare distances between the reference marks to distances between corresponding components and synchronize a feed rate of the components to a feed rate of the first layer. After adhering the components to the first layer, the positions of the components relative to the reference marks are once again checked and, if necessary, the setpoint for the feed rate of the components is adjusted.

2 Claims, 11 Drawing Sheets

U.S. PATENT DOCUMENTS

| | | | |
|---|---|---|---|
| 4,315,508 A | 2/1982 | Bolick | 128/289 |
| 4,316,566 A | 2/1982 | Arleth et al. | 226/2 |
| 4,322,026 A | 3/1982 | Young, Jr. | 226/15 |
| 4,349,997 A | 9/1982 | Hayasaka et al. | 53/51 |
| 4,392,910 A | 7/1983 | Tokuno et al. | 156/361 |
| 4,397,704 A | 8/1983 | Frick | 156/201 |
| 4,397,709 A | 8/1983 | Schwenzer | 156/351 |
| 4,400,230 A | 8/1983 | Wyslotsky | 156/361 |
| 4,417,935 A | 11/1983 | Spencer | 156/80 |
| 4,496,417 A | 1/1985 | Haake et al. | 156/361 |
| 4,543,141 A | 9/1985 | Bradley et al. | 156/164 |
| 4,549,917 A | 10/1985 | Jensen, Jr. | 156/108 |
| 4,572,752 A | 2/1986 | Jensen et al. | 156/64 |
| 4,576,663 A | 3/1986 | Bory | 156/64 |
| 4,610,739 A | 9/1986 | Jensen | 156/64 |
| 4,615,695 A | 10/1986 | Cooper | 604/385 A |
| 4,662,875 A | 5/1987 | Hirotsu et al. | 604/389 |
| 4,680,080 A * | 7/1987 | Instance | 156/357 |
| 4,704,171 A | 11/1987 | Thompson et al. | 156/64 |
| 4,711,683 A | 12/1987 | Merkatoris | 156/164 |
| 4,795,513 A | 1/1989 | Jensen, Jr. | 156/108 |
| 4,819,406 A | 4/1989 | Redmond | 53/51 |
| 4,837,715 A | 6/1989 | Ungpiyakul et al. | 364/552 |
| 4,883,549 A | 11/1989 | Frost et al. | 156/161 |
| 4,888,717 A | 12/1989 | Ditto et al. | 364/559 |
| 4,909,879 A | 3/1990 | Ball | 156/164 |
| 4,935,087 A | 6/1990 | Gilman | 156/251 |
| 4,940,464 A | 7/1990 | Van Gompel et al. | 604/396 |
| 5,045,135 A | 9/1991 | Meissner et al. | 156/64 |
| 5,046,272 A | 9/1991 | Vogt et al. | 38/143 |
| 5,094,708 A | 3/1992 | Bechtel et al. | 156/351 |
| 5,104,116 A | 4/1992 | Pohjola | 271/185 |
| 5,162,066 A | 11/1992 | Martensson et al. | 156/163 |
| 5,185,055 A | 2/1993 | Temple et al. | 156/630 |
| 5,200,020 A | 4/1993 | Collins et al. | 156/520 |
| 5,221,058 A | 6/1993 | Fillis | 242/57.1 |
| 5,224,405 A | 7/1993 | Pohjola | 83/24 |
| 5,235,515 A | 8/1993 | Ungpiyakul et al. | 364/469 |
| 5,269,123 A | 12/1993 | Marchesini | 53/559 |
| 5,304,272 A | 4/1994 | Rohrbacker et al. | 156/209 |
| 5,359,525 A | 10/1994 | Weyenberg | 364/469 |
| 5,366,791 A | 11/1994 | Carr et al. | 428/195 |
| 5,383,988 A | 1/1995 | Herrmann et al. | 156/64 |
| 5,389,093 A | 2/1995 | Howell | 604/361 |
| 5,470,411 A | 11/1995 | Gloton et al. | 156/64 |
| 5,483,893 A | 1/1996 | Isaac et al. | 101/485 |
| 5,492,591 A | 2/1996 | Herrmann et al. | 156/538 |
| 5,575,782 A | 11/1996 | Hasse et al. | 604/385.1 |
| 5,591,152 A | 1/1997 | Buell et al. | 604/385.2 |
| 5,766,389 A | 6/1998 | Brandon et al. | 156/64 |
| 5,818,719 A | 10/1998 | Brandon et al. | 364/469.04 |
| 5,930,139 A | 7/1999 | Chapdelaine et al. | 364/468.25 |
| 5,932,039 A | 8/1999 | Popp et al. | 156/64 |

FOREIGN PATENT DOCUMENTS

| | | | |
|---|---|---|---|
| CA | 2016529 | 11/1990 | B32B/3/00 |
| CA | 1283814 | 5/1991 | A61F/13/15 |
| CA | 1287295 | 8/1991 | B65B/9/04 |
| CA | 2044792 | 5/1992 | G05D/5/04 |
| CA | 2115455 | 3/1993 | E04C/2/24 |
| CA | 2121140 | 4/1993 | B32B/3/00 |
| CA | 2084837 | 6/1993 | B32B/3/10 |
| CA | 1336256 | 7/1995 | B32B/31/18 |
| EP | 009 739 | 4/1980 | B65C/3/16 |
| EP | 011 967 | 6/1980 | B65C/9/42 |
| EP | 547 497 | 6/1993 | A61F/13/15 |
| EP | 589 859 | 3/1994 | A61F/13/15 |
| EP | 737 638 | 10/1996 | B65H/23/188 |
| FR | 2 559 037 | 2/1984 | A41B/13/02 |
| FR | 148 115 | 11/1984 | A41B/13/02 |
| GB | 2 170 486 | 8/1986 | B65H/39/16 |
| JP | 58 201611 | 11/1983 | B29C/27/00 |
| JP | 58220039 | 12/1983 | B65H/25/24 |
| JP | 63-5927 | 1/1988 | |
| WO | 03089 | 5/1988 | B32B/31/18 |
| WO | 11886 | 10/1990 | B31F/1/20 |
| WO | 11887 | 10/1990 | B31F/1/28 |
| WO | 08789 | 4/1994 | B32B/31/08 |
| WO | 18590 | 7/1995 | A61F/13/15 |
| WO | 24094 | 7/1997 | A61F/13/15 |
| WO | 24283 | 7/1997 | B65H/39/16 |
| WO | 21134 | 5/1998 | B65H/39/14 |

* cited by examiner

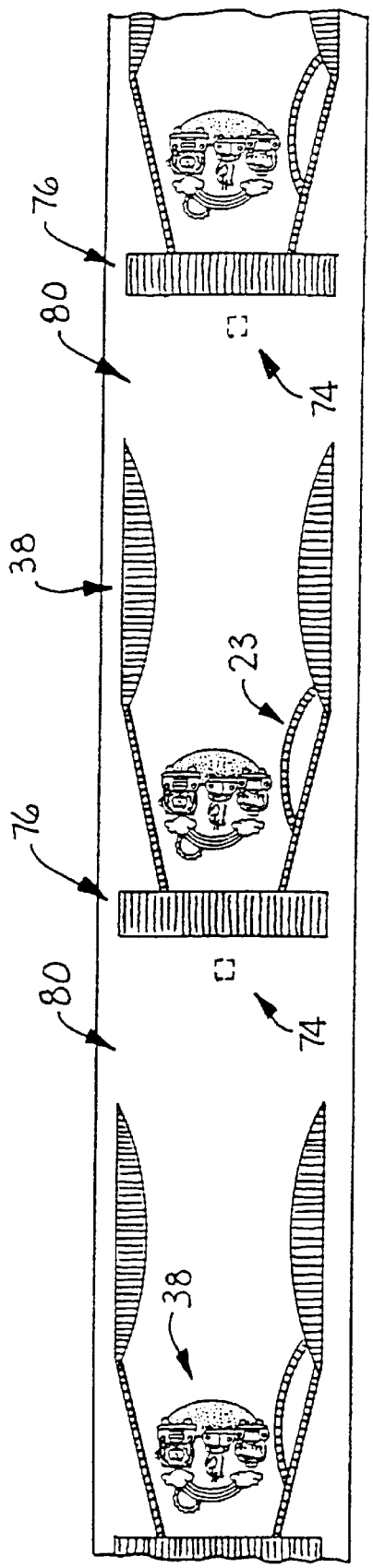
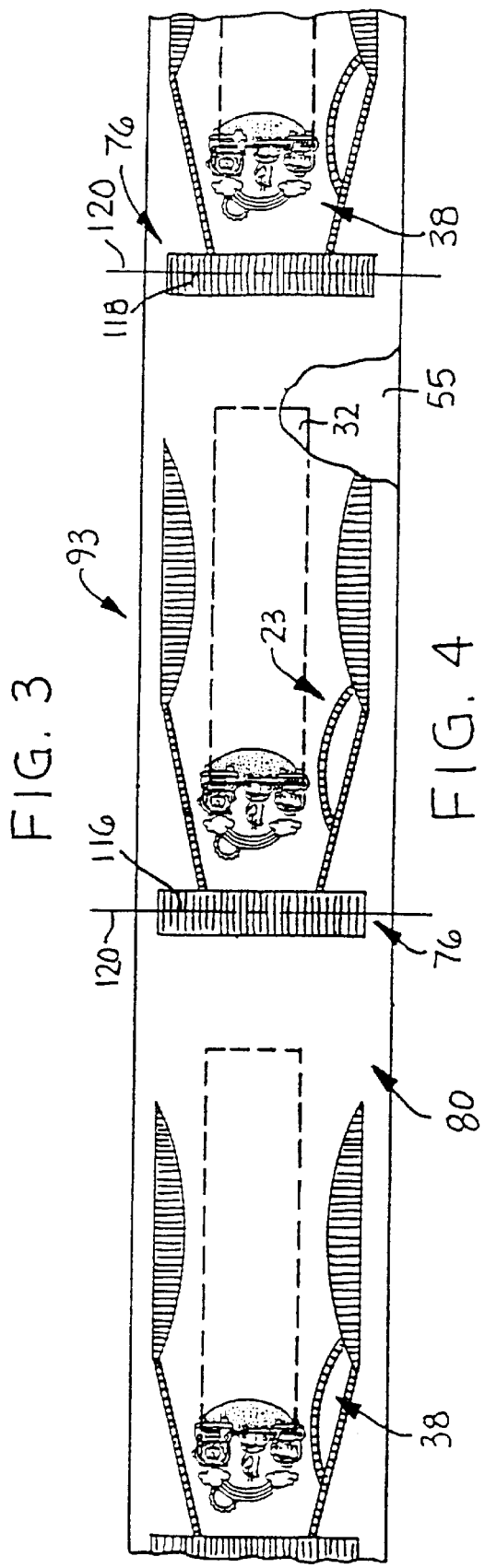
FIG. 3
FIG. 4

PROCESSES AND APPARATUS FOR MAKING DISPOSABLE ABSORBENT ARTICLES

This application claims the benefit of Provisional Application No. 60/118,988, filed Feb. 8, 1999.

The present invention relates to processes and apparatus for making articles, and particularly to processes and apparatus for making disposable absorbent articles.

BACKGROUND OF THE INVENTION

Disposable absorbent products can be fabricated in a continuous production line by the sequential addition of components to previously supplied components. This is particularly advantageous when one or more of the components can be supplied in the form of a single continuous layer. For example, in the formation of disposable absorbent articles, such as training pants, absorbent pants, diapers, incontinence articles, feminine care products, or the like, a layer is normally supplied at a point in the fabrication line in the form of a continuous roll, and absorbent pads, waist elastic bands, leg elastic bands, stretchable side panels, and/or other components can be supplied at different points in the fabrication line as discrete elements.

Various processes and apparatus are available for bringing the components of a single product together so that the components in the composite product are in a desired relation with respect to each other. In bringing these components properly together, various known processes and apparatus are used to note the position of a particular component, and then to adjust the position of subsequent components in order to properly position them.

A problem encountered with these types of processes and apparatus is that they do not adequately compensate for the stretching, or other possibly occurring defects, of a continuously moving layer. During manufacturing processes of this type, a continuously moving layer is subjected to various tensions caused by it being driven or pulled through the process for handling. This tension causes the continuously moving layer to stretch, or to relax, thereby resulting in some components being undesirably positioned or, once positioned, shifted out of position. Since it is virtually impossible to maintain a constant tension on the continuously moving layer, the degree of stretching varies throughout the process. Consequently, even though an earlier positioned component may initially be within an acceptable position range, the stretching, by way of example, of the continuously moving layer may result in the component being outside of the acceptable position range in the final composite product. Other undesirable occurrences may also result in mis-registration of a component or components.

SUMMARY OF THE INVENTION

In response to the discussed difficulties and problems encountered in the prior art, a new process and apparatus for making a disposable absorbent article, and in particular one having a registered graphic, has been discovered.

The present invention will be described herein in the context of registering and controlling the registration of a continuously moving layer and discrete components with respect to that continuously moving layer in the manufacture of disposable absorbent articles or products, such as, by way of example, a child's training pant. Examples of other disposable absorbent articles include, but are not limited to, diapers, feminine care products, incontinence products, or the like. The terms "registered," "registering" and "registration" refer to aligning objects with respect to one another, or adjusting the alignment of objects with respect to one another to achieve proper alignment. The term "component" can refer, but is not limited to, elastic ribbons or strips, absorbent pads, containment flaps, stretchable or non-stretchable layers, adhesive patterns, portions thereof, or the like; or a graphic. The term "graphic" can refer, but is not limited to, any design, pattern, or the like.

A child's disposable training pant can have multiple appearance-related and/or functional components registered within selected machine direction (MD) and/or cross-machine direction (CD) ranges. The term "machine direction" refers to the primary direction of movement of continuously moving layers in the manufacturing process, and the term "cross-machine direction" refers to the direction substantially normal to the machine direction.

The present invention can provide, by way of example, a child's disposable training pant having one or more appearance-related and/or functional components registered with other components. Examples of components that are appearance-related include, but are not limited to, the registration of graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

Examples of functional components include, but are not limited to, absorbent pads, surge or acquisition layers, side panels, tapes, containment flaps, waist elastics, leg elastics, areas of breathability, fluid repellent areas, fluid wettable areas, adhesives or coatings, encapsulated inks, chemically-sensitive materials, environmentally-sensitive materials, heat-sensitive materials, moisture-sensitive materials, perfumes, odor control agents, inks, fasteners, fluid storage areas, textured or embossed areas, or the like.

The training pant described herein, by way of example, comprises an absorbent pad positioned between a liquid impermeable outer cover and a liquid permeable liner. The training pant further includes elastic side panels which are joined to the outer cover in order to provide elasticity thereto. The liquid impermeable outer cover can comprise two layers of material suitably joined together, in which the innermost layer can be a liquid impermeable layer and the outermost layer can be a nonwoven layer having cloth-like texture. The innermost liquid impermeable layer has a graphic printed in registration thereon. The registered graphic generally includes a visually pleasing design or pattern and is controllably registered at a designated area in the product. One registered graphic includes a graphic positioned on the front center of the product. A more detailed description of the construction and design of the above-described training pant can be found in U.S. Pat. No. 4,940,464 issued Jul. 10, 1990 to Van Gompel et al., which is incorporated herein by reference.

Described herein is a distinctive process and apparatus for registering discrete components to a continuously moving first layer. The first layer of material includes one or more reference marks provided thereon at a uniform repeat length. This uniform repeat length can be, but is not limited to, a machine product repeat length which is the length of one product during the manufacturing process. Hereinafter, the uniform repeat length is a machine product repeat length for purposes of description, but the present invention contemplates other lengths or dimensions that could serve as a uniform repeat length. The distance between two successive reference marks is determined and then used to calculate a desired speed and/or placement for adding other components to the process.

The term "reference mark" can refer, but is not limited, to a component or components or portions thereof such as elastic strips, absorbent pads, adhesive patterns, or the like; structure such as corners or edges thereof, transporting mediums such as conveyor belts or the like; visual marks, magnetic marks, electrical marks, electromagnetic marks, optical brighteners sensitive to ultraviolet radiation, or the like. All of these can be sensed, detected, or otherwise identified by an appropriate device.

The reference marks determine product length and the product per minute speed while the web speed (feet per minute) remains constant. The reference marks provide placement references which are used to generate reference signals with which the other product components can be controlled and/or registered. Since a component can serve as a reference mark, it may be identified or described as a "component-reference mark".

The first layer can have selectively provided thereon reference marks corresponding to a respective plurality of distinct and separate locations on the layer or components. For purposes of this embodiment, the first component comprises a plurality of graphics. A first sensor generates a signal in response to each reference mark. The distance between consecutive reference mark signals is suitably measured in units of, by way of example, a driving mechanism, such as a lineshaft registration encoder. This measurement is the first component repeat length or machine product repeat length.

A second component is added to the first layer by a machine module having its own driving mechanism. The second component could be laid relative to a reference mark or the first component. A second sensor associated with this second component to be registered generates a second signal referred to as a second component signal in response to each second component that serves as a component-reference mark. The distance between consecutive second component signals is also measured in units of the same driving mechanism as the first layer, such as the lineshaft registration encoder. This measurement is the second component repeat length.

The ratio of a second component repeat length to a machine product repeat length is a gear ratio which is used to calculate a speed reference signal for speed control, so that the speed of the second component driving mechanism can be selectively controlled to adjust the speed and/or placement of a second component, such that the distance between subsequent consecutive second component signals is one machine product repeat length. This provides one second component repeat length in one machine product repeat length and is called a repeat loop. The repeat loop refers to repeatedly providing a second component at a rate substantially equal to the rate of the first layer, thereby duplicating a machine product repeat length between two successive reference marks by accurately measuring their current distance apart and calculating a desired speed reference signal for a component driving mechanism.

The second component also is controllably positioned with respect to a reference mark of the first layer. This is termed the placement loop and is performed by comparing the measured distance between a component signal and its corresponding reference mark signal to the target setpoint, and then adjusting the position of future second components to the setpoint. A "target setpoint" refers to a selected value to which the placement is controlled. A "component signal" is generated from a sensor detecting components or reference marks on the second layer. A "reference mark signal" is generated from a sensor detecting reference marks on the first layer.

Thus, there is described herein, by way of example, a process and an apparatus for using a first layer of material, which may include one or more distinct and separate components pre-positioned thereon, and providing a simplified device for registering other components on the first layer, thereby ultimately providing individual disposable absorbent articles. One process of the present invention uses consistently placed or positioned reference marks on the continuous first layer to generate reference signals throughout the entire manufacturing process.

One advantage of the process and apparatus is that it provides a unique machine product repeat length change capability during the manufacturing process by providing the ability to automatically change the speed and/or feed rate of various modules that provide selected components. Thus, the speed, registration, and other desired changes needed for a machine product repeat length change for, by way of example, manufacturing different sizes or types of products, can be accomplished by changing the first layer with another layer having a different length between reference marks, in which the different length corresponds to the change in product size or type. The present invention automatically senses these changes and controllably adjusts the repeat loop and the placement loop for other components.

The first layer of material can be, for example, a continuous polyethylene film preprinted with one or more reference marks per product. The use of the term "layer" can refer, but is not limited, to any type of substrate, such as a woven web, nonwoven web, films, laminates, panels, composites, elastomeric materials, or the like. A layer can be liquid and air permeable, permeable to air and impermeable to liquids, impermeable both to air and liquid, or the like. The reference marks are preprinted or otherwise arranged such that they will be positioned at the same designated area in each finished product. The term "finished" or "final", when used with reference to a product, means that the product has been suitably manufactured for its intended purpose.

The process of the present invention senses the first layer's reference marks that are moving at a desired constant rate of speed and generates a reference signal for other machine components and modules. In particular, there is provided accurate, real time information during the production process, and rapid adjustments to the process to provide the desired registration of subsequent components in the final products. Additionally, process control variables can be automatically modified in response to changes in machine product repeat length in accordance with preprogrammed instructions.

Earlier, a reference mark was described with some examples. In the embodiments described hereinafter, the reference mark selected is an optical brightener which can be configured in any desired size or shape. The reference mark may comprise, for instance, a generally rectangular region having a machine direction dimension of about 19 millimeters and a cross-machine direction dimension of about 37 millimeters. Optionally, other dimensions may be employed. It is to be understood that the various detecting and sensing devices described herein are to be appropriately compatible with the type of associated reference mark that is to be detected or sensed. The term "associated" refers to the reference mark either being directly on a component that it represents, such as a graphic, or being selectively spaced therefrom. The optical brightener is provided to be sensitive to ultraviolet radiation. The optical brightener is, for example, capable of absorbing ultraviolet radiation and then fluorescing to emit light spectra that can be sensed by an appropriate and compatible detector or sensor. Ultraviolet radiation is generally understood to include electromagnetic radiation having wave lengths ranging from about 20–400 nanometers. Suitable optical brighteners include, for example, UVITEX OB manufactured by Ciba-Geigy, and LEUCOPURE EGM manufactured by Sandoz Chemicals Corporation.

Where the reference mark comprises ultraviolet sensitive optical brighteners, a suitable detector or sensor is a UV activated detector, such as a SICK detector model LUT 3-6 available from SICK OPTIK ELEKTRONIK, Inc., a business having offices in St. Paul, Minn.

Other suitable reference marks, as well as sensors, computer devices, motors, and the like are described in U.S. Pat. No. 5,235,515 issued Aug. 10, 1993 to Ungpiyakul et al.; U.S. Pat. No. 5,359,525 issued Oct. 25, 1994 to Weyenberg; and U.S. Pat. No. 4,837,715 issued Jun. 6, 1989 to Ungpiyakul et al.; the contents of each of which are incorporated herein by reference.

The described process and apparatus utilize several devices, and representative devices include encoders, signal counters, and sensors or detectors. An encoder generates a pulse train, which is a selected number of pulses per revolution of the encoder shaft, for subsequent counting and control. A signal counter receives a generated pulse train from an encoder, and counts the pulses for subsequent query. A sensor or detector senses an occurrence or interruption in a process and generates a signal in response thereto.

BRIEF DESCRIPTION OF THE DRAWINGS

The above-mentioned and other features of the present invention and the manner of attaining them will become more apparent, and the invention itself will be better understood by reference to the following description and the a accompanying drawings, wherein similar features in different figures have been given the same reference numeral.

FIG. 3 illustrates a continuously moving layer having a plurality of separate and distinct graphics thereon.

FIG. 4 illustrates a continuously moving composite layer having a plurality of separate and distinct components thereon.

DETAILED DESCRIPTION OF THE PRESENTLY PREFERRED EMBODIMENTS

Figure 1:
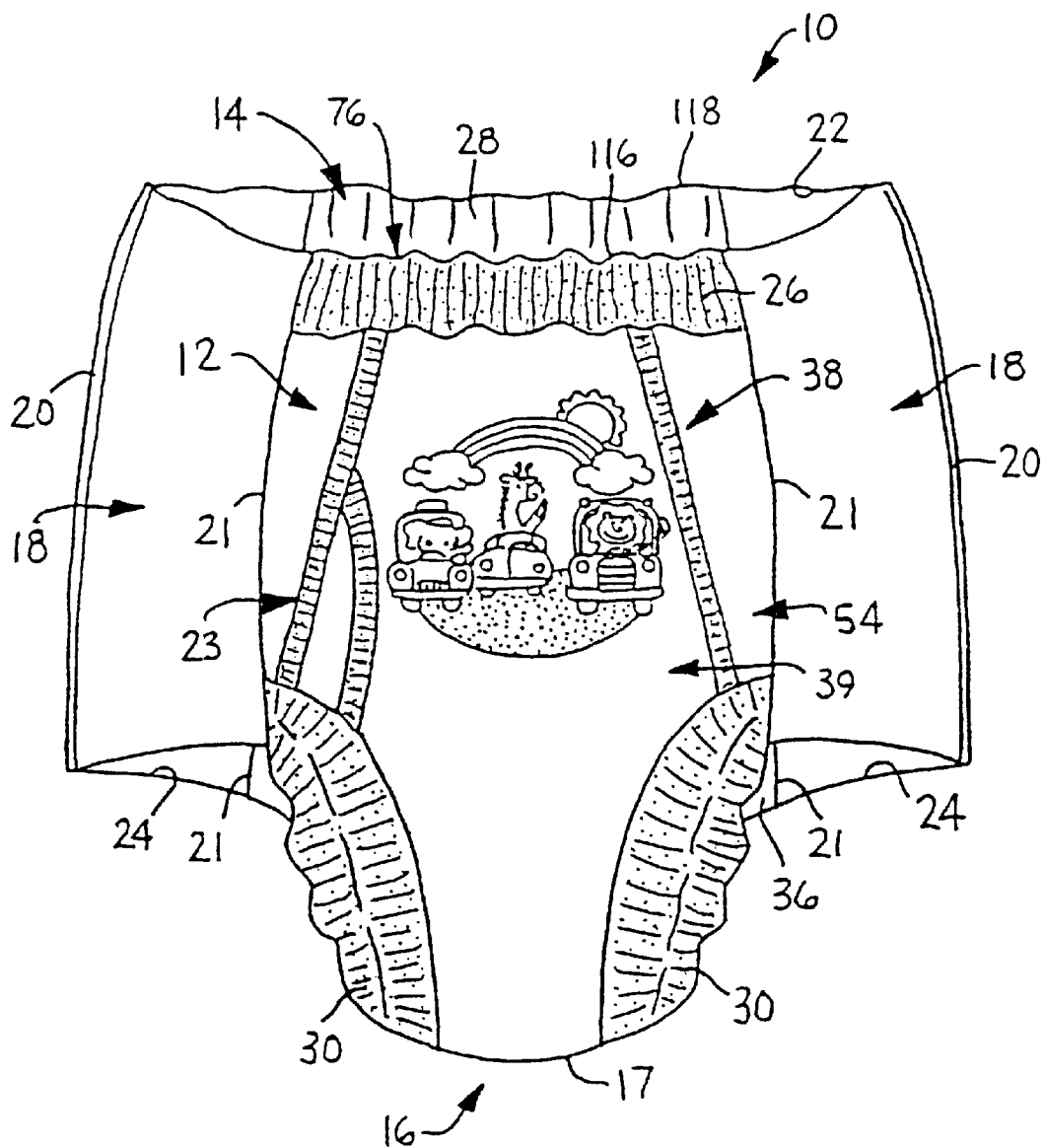
FIG. 1 illustrates a front view of one disposable absorbent article.

Referring now to FIG. 1, there is illustrated a child's disposable training pant 10 generally comprising a front panel 12, a back panel 14, a crotch panel 16 interconnecting front and back panels 12 and 14, and a pair of elastic side panels 18. Each elastic side panel 18 is formed from two separate elastic portions 19 (FIG. 2A) and are suitably joined together, such as by ultrasonic bonding, to form a side seam 20. Upon the construction of side seams 20, a waist opening 22 and leg openings 24 are formed. The side seams 20 may be constructed to be manually tearable in order to allow training pant 10 to be disassembled manually by the caregiver, so that it can be easily removed from the child, for example, after a bowel movement. The elastic side panels 18 and side seams 20 can be provided in any suitable manner. One specific manner of supplying elastic side panels 18 is described in U.S. Pat. No. 5,224,405 issued Jul. 6, 1993 and U.S. Pat. No. 5,104,116 issued Apr. 14, 1992, both to Pohjola, which are incorporated herein by reference. The provision of side seams 20 can be accomplished in the manner described in U.S. Pat. No. 5,046,272 issued Sep. 10, 1991 to Vogt et al., which is incorporated herein by reference.

The training pant 10 further comprises a front waist elastic 26 suitably Joined to front panel 12, a back waist elastic 28 suitably joined to back panel 14, leg elastics 30 suitably joined to crotch panel 16, and an absorbent pad 32 (FIG. 4) positioned between a liquid impermeable outer cover or backsheet 54 (FIG. 1) and a liquid permeable liner or topsheet 36 (FIG. 1). The basic construction of a training pant is well known in the art, and one particular construction is that described in U.S. Pat. No. 4,940,464 issued Jul. 10, 1990 to Van Gompel et al., the contents of which are incorporated herein by reference. This patent to Van Gompel et al. also describes various materials of which a training pant can be made, and a method of constructing the training pant.

As illustrated in FIG. 1, a component such as a graphic 38 is selectively positioned and registered on front panel 12, and in this illustration comprises a design of a rainbow, sun, clouds, cars, and a simulated "fly opening" 23 typical of a boy's underwear. The registered graphic 38 can be any type of desired pattern, artistic feature, written instructions, or the like, and is desired to be positioned in the article at a selected location. Naturally, registered graphic 38 comprising a simulated fly opening 23 would be totally unacceptable from an aesthetic and/or functional viewpoint if it were located at crotch panel 16 or back panel 14.

Figure 2:
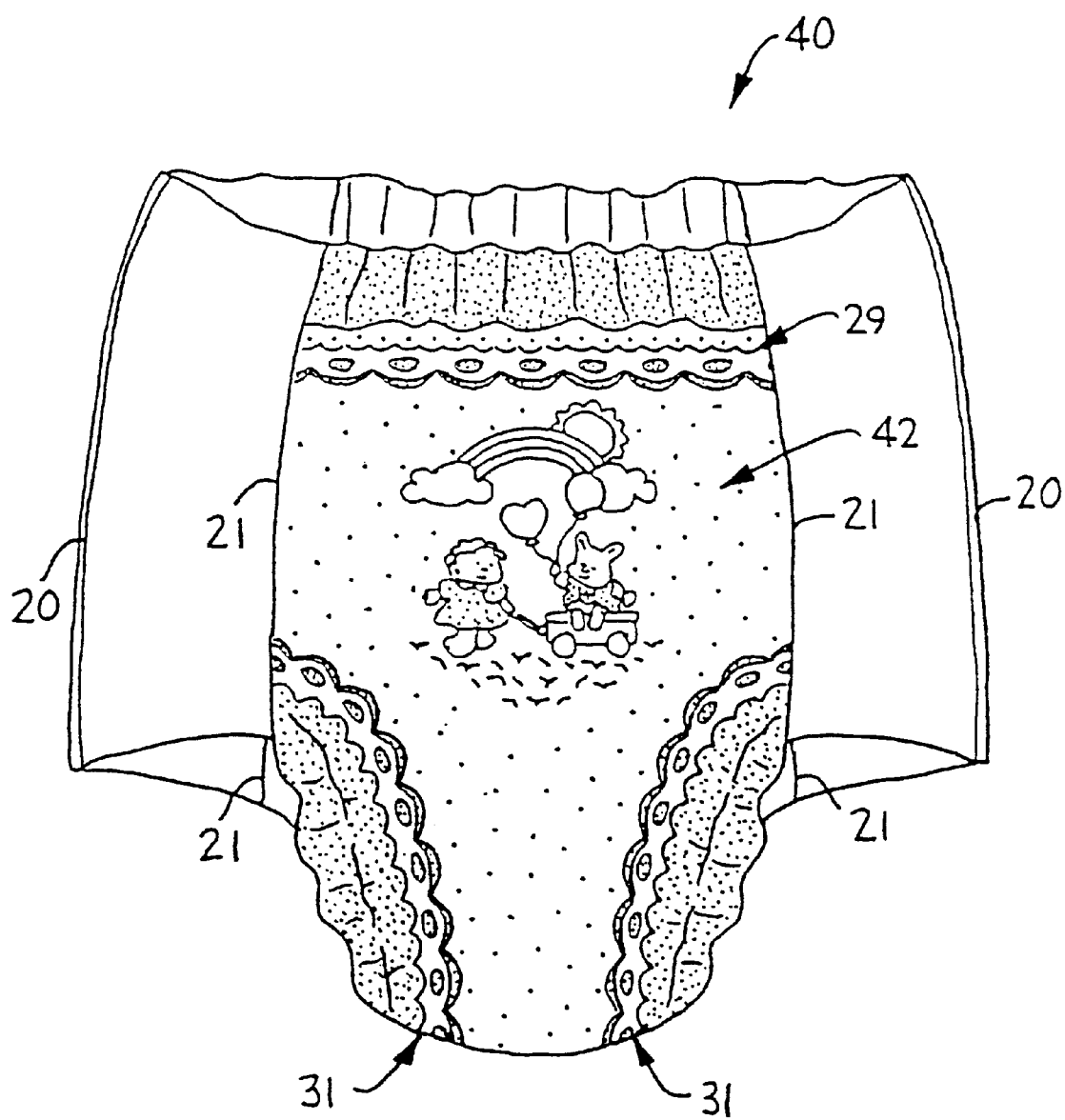
FIG. 2 illustrates a front view of another disposable absorbent article, which is similar to that of FIG. 1 but designed for a girl rather than boy wearer.

Referring to FIG. 2, another training pant 40 is illustrated, which can be typically used for young girls. In this design, a registered graphic 42 includes simulated waist ruffles 29, simulated leg ruffles 31, a rainbow, sun, clouds, wagon and balloon. Again, any suitable design can be utilized for a training pant intended for use by young girls, so as to be aesthetically and/or functionally pleasing to them and the caregiver.

The graphic 38 in FIG. 1 or the graphic 42 in FIG. 2 can be selectively positioned or registered as desired, depending upon the size and shape of the graphic and that portion of the product upon which the graphic is to be positioned. In FIG. 1, the graphic 38 is selectively positioned or registered within a designated area 39 which, as viewed in FIG. 1, is bounded or defined by a front waist edge 116, panel seams 21, and a crotch panel line 17. The panel seams 21 are the seams at which the respective elastic side panels 18 are suitably joined to front panel 12 and back panel 14. Again, a more specific description of the construction and manufacture of this design of a training pant 10 is contained in the aforementioned U.S. Pat. No. 4,940,464 to Van Gompel et al. The crotch panel line 17 is, for purposes of explanation herein, simply the line or boundary formed at the bottom of crotch panel 16 as illustrated in FIG. 1. Thus described, designated area 39 has four defined boundaries comprising front waist edge 116, panel seams 21, crotch panel line 17, and those portions of leg openings 24 extending between a respective panel seam 21 and crotch panel line 17. It is not necessary that a designated area 39 be completely defined or bounded by a closed line or closed boundary. For example, in FIG. 1, the designated area 39 could be defined by only front waist edge 116 and the panel seams 21, which sufficiently defines a designated area 39 in which a graphic 38 can be selectively registered or positioned. In this case, the graphic 38 can be selectively registered or positioned a selected distance from the front waist edge 116 and centered between the panel seams 21.

Figure 2A:
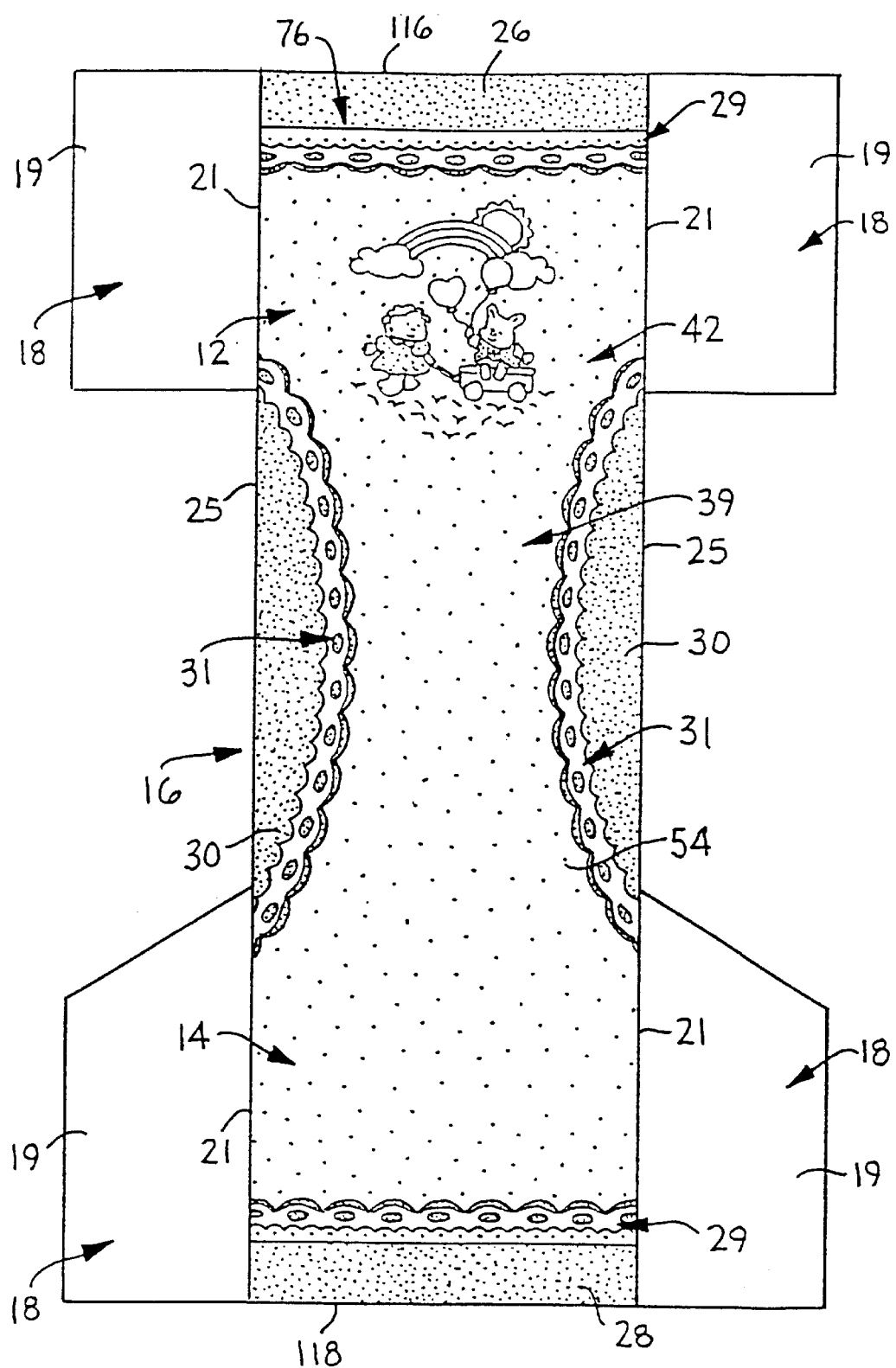
FIG. 2A representatively illustrates the article of FIG. 2 in a partially disassembled, stretched flat state.

Another example of the flexibility in choosing a designated area 39 is illustrated in FIG. 2A, which illustrates the training pant 40 in FIG. 2 in a partially disassembled, stretched flat state. This can be accomplished by taking the finished training pant 40 of FIG. 2 and manually tearing seams 20 and then laying the pant 40 flat and stretching it sufficiently to remove any gathers or pleating caused by any incorporated elastic members. In FIG. 2A, the designated area 39 is defined or bounded by front waist edge 116, panel seams 21, back waist edge 118, and a pair of leg opening edges 25 extending between respective panel seams 21. Thus, in FIG. 2A, the designated area 39 is generally rectangular in shape, and the graphic 42 is selectively registered or positioned within and throughout the surface area of the designated area 39. The graphic 42 comprises several component designs, such as simulated leg ruffles 31 and simulated waist ruffles 29. As viewed in FIG. 2A, leg opening edges 25 are linear or straight lines. However, in FIG. 2, simulated leg ruffles 31 provide a perceived curvature or shape to training pant 40, which is a desirable feature that may be provided hereby.

There is uniquely and advantageously provided a very close tolerance in the registration or position of a component, such as the graphics 38 and 42, within any selected point or area, such as designated area 39. With reference to FIG. 1, it is apparent that the simulated fly opening 23 of graphic 38 needs to be registered or positioned within front panel 12. It would be undesirable to have training pant 10 manufactured by a method and/or apparatus that could not control the proper registration or position of the simulated fly opening 23, otherwise the simulated fly opening 23 could appear at the back panel 14 or crotch panel 16. The present invention provides a highly controlled registration or position of all components, such as, by way of example, the graphic 38 or 42, the front waist elastic 26, the back waist elastic 28, the leg elastics 30, the absorbent pad 32 (FIG. 4), or the like, within a desired designated position or area, such as designated area 39. Tolerances of about plus or minus 25 millimeters or less, and more particularly tolerances between about plus or minus 3 millimeters or less, are attainable in the registration of components.

Figure 5A:
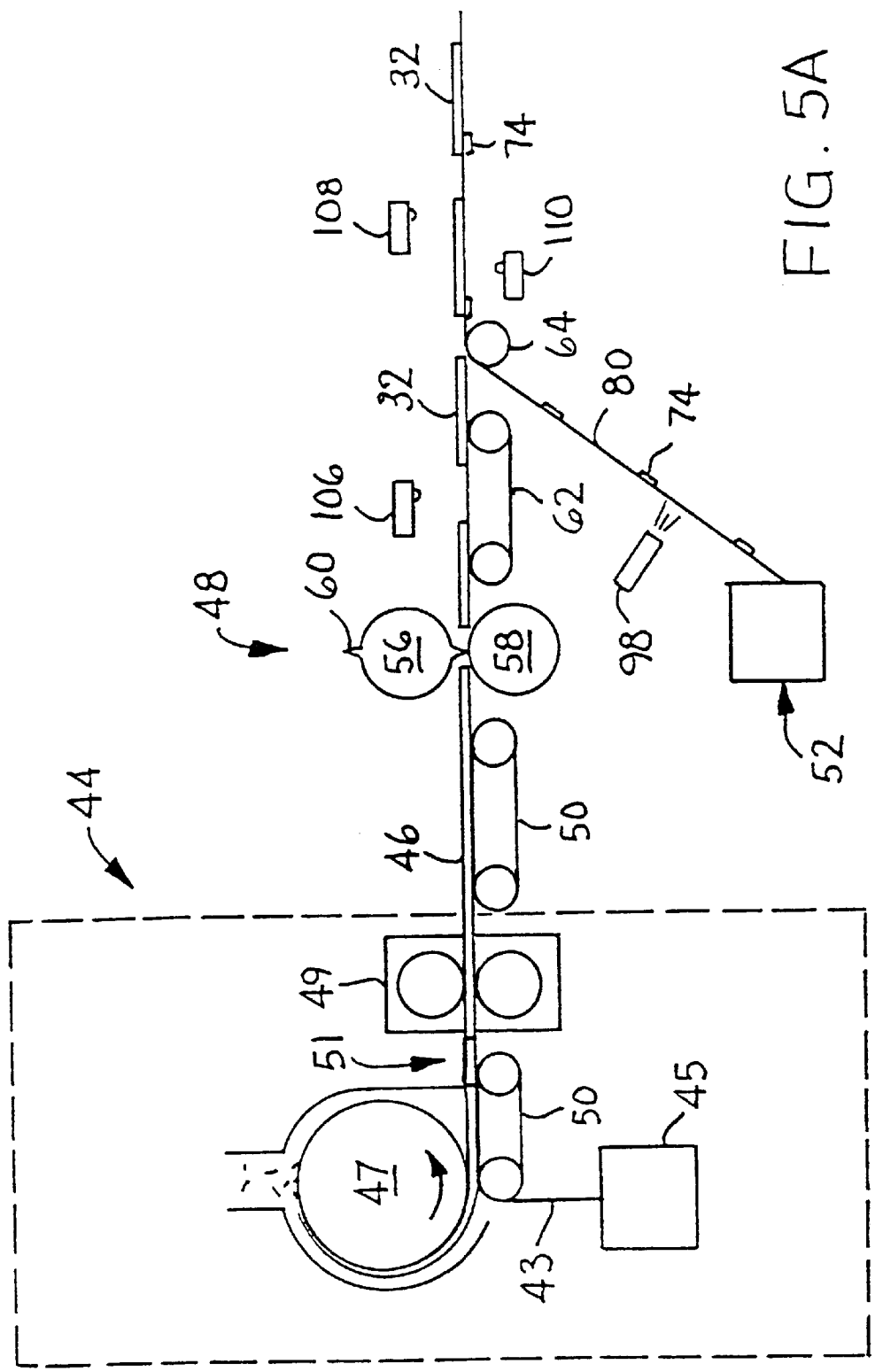
FIG. 5A partially illustrates schematically the upstream or left portion of one apparatus and process for the manufacture of a disposable absorbent article including registered components.
Figure 5B:
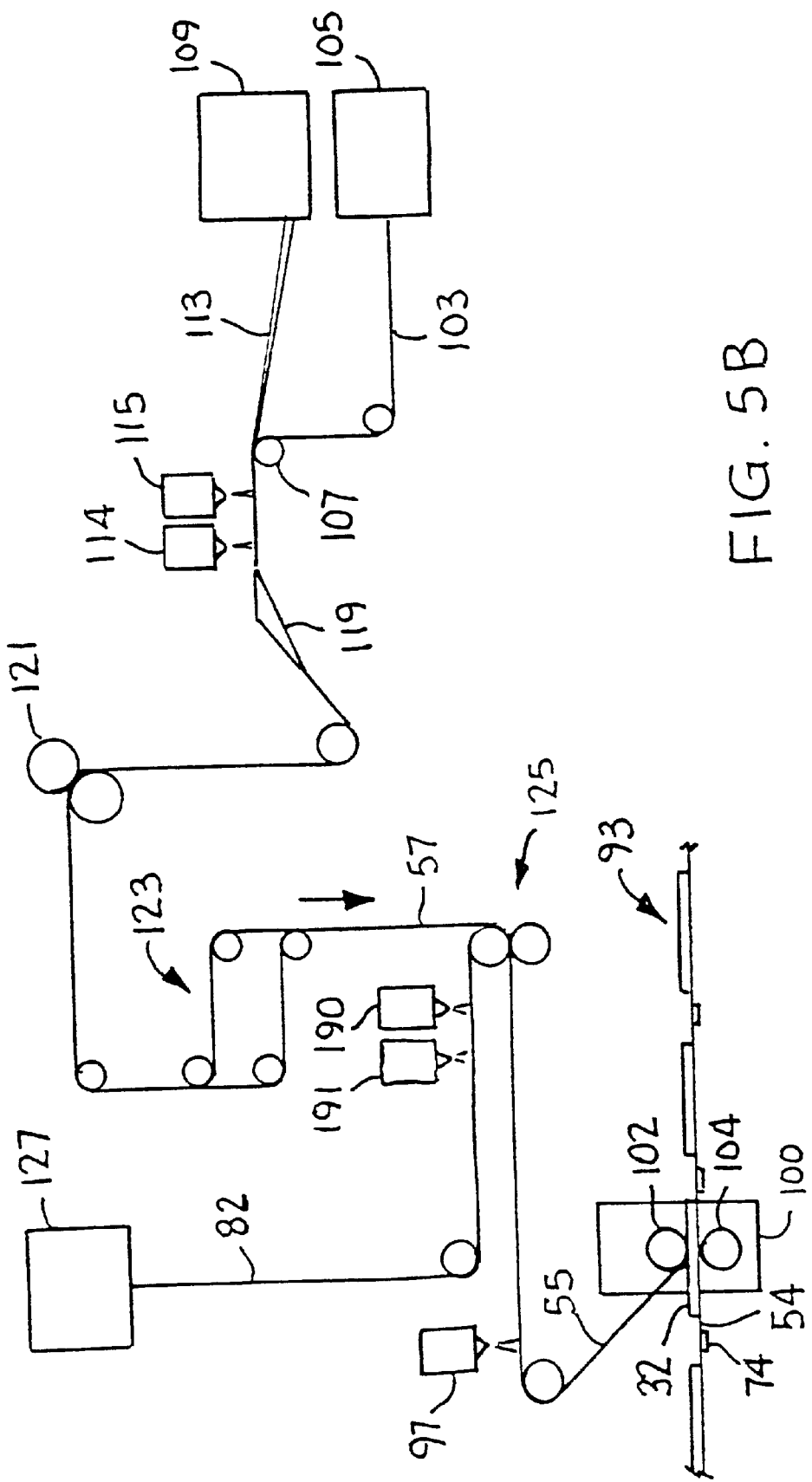
FIG. 5B illustrates schematically the downstream or right portion of the apparatus and process partially shown in FIG. 5A.

Referring now to FIGS. 5A and 5B, there is schematically shown an apparatus and process of the present invention for assembling portions of a plurality of training pants. A supply device 44 continuously supplies a continuous, tissue-wrapped absorbent 46 to a separating device 48 that separates the continuous, tissue-wrapped absorbent 46 into a plurality of distinct and separate absorbent pads 32. The supply device 44 can include any conventional mechanism for supplying the absorbent 46. Generally, a conventional supply device 44 will include a hammermill for forming fluff fibers and, if desired, for providing an enclosure for mixing superabsorbent material with the fluff fibers, and then depositing the fluff and superabsorbent material on a forming drum 47 having a desired absorbent shape. The forming drum 47 then deposits the shaped absorbent on a continuously moving tissue layer 43 provided by supply device 45, which is thereafter delivered to a conventional wrap sheet folder assembly 51 for folding the tissue about the absorbent. The supply device 45 can be any suitable mechanism, such as a pair of spindles, a festoon assembly, and a dancer roll for providing tissue layer 43 at a desired speed and tension.

A conveyor 50, which can be any conventional conveyor well known in the art, conveys the absorbent 46 to the separating device 48. The tissue-wrapped absorbent 46 may be debulked by passing it through a pair of nip rolls in debulker assembly 49.

The absorbent can include any desired mixture or blend of absorbing materials, such as fluff and superabsorbent materials. Suitable superabsorbent materials are available from various commercial vendors such as Dow Chemical Company, Hoechst-Celanese Corporation and Allied Colloids, Inc. Typically, a superabsorbent material is capable of absorbing at least about 15 times its weight in water, and desirably more than about 25 times its weight in water.

A supply device 52 provides a continuously moving first layer of material 80, upon which can be disposed or positioned any desired component, such as the separate and distinct absorbent pads 32 formed by separating device 48. The supply device 52 can be any standard unwind mechanism that generally comprises, for example, a pair of spindles, a festoon assembly, and a dancer roll for providing first layer 80 at a desired speed and tension. One example of a standard unwind is a model MB 820, available from Martin Automatic Corporation of Rockford, Ill.

The continuously moving first layer of material 80 can be any desired material suitable for the particular product or components being assembled. In this description of a training pant 10 or 40 (FIGS. 1 and 2), the continuously moving first layer 80 is a liquid impermeable material that will subsequently form or become the liquid impermeable outer cover or backsheet 54. One suitable liquid impermeable film is a 0.75 mil polyethylene film commercially available from Huntsman Packaging, with offices in Kent, Washington.

The continuous, tissue-wrapped absorbent 46 is cut into the separate and distinct absorbent pads 32 by the separating device 48. In the illustrated embodiment, the separating device 48 comprises a knife roll 56 and an anvil roll 58 that are operatively associated with one another. The knife roll 56 can have any desired number of blades thereon, and in this example has two blades 60 diametrically disposed thereon for forming absorbent pads 32. A pad transfer conveyor 62 or other suitable device may be used to convey the absorbent pads 32 toward a mating roll 64, whereupon the distinct and separate absorbent pads 32 formed by the separating device 48 are placed upon the continuously moving first layer 80.

Figure 6:
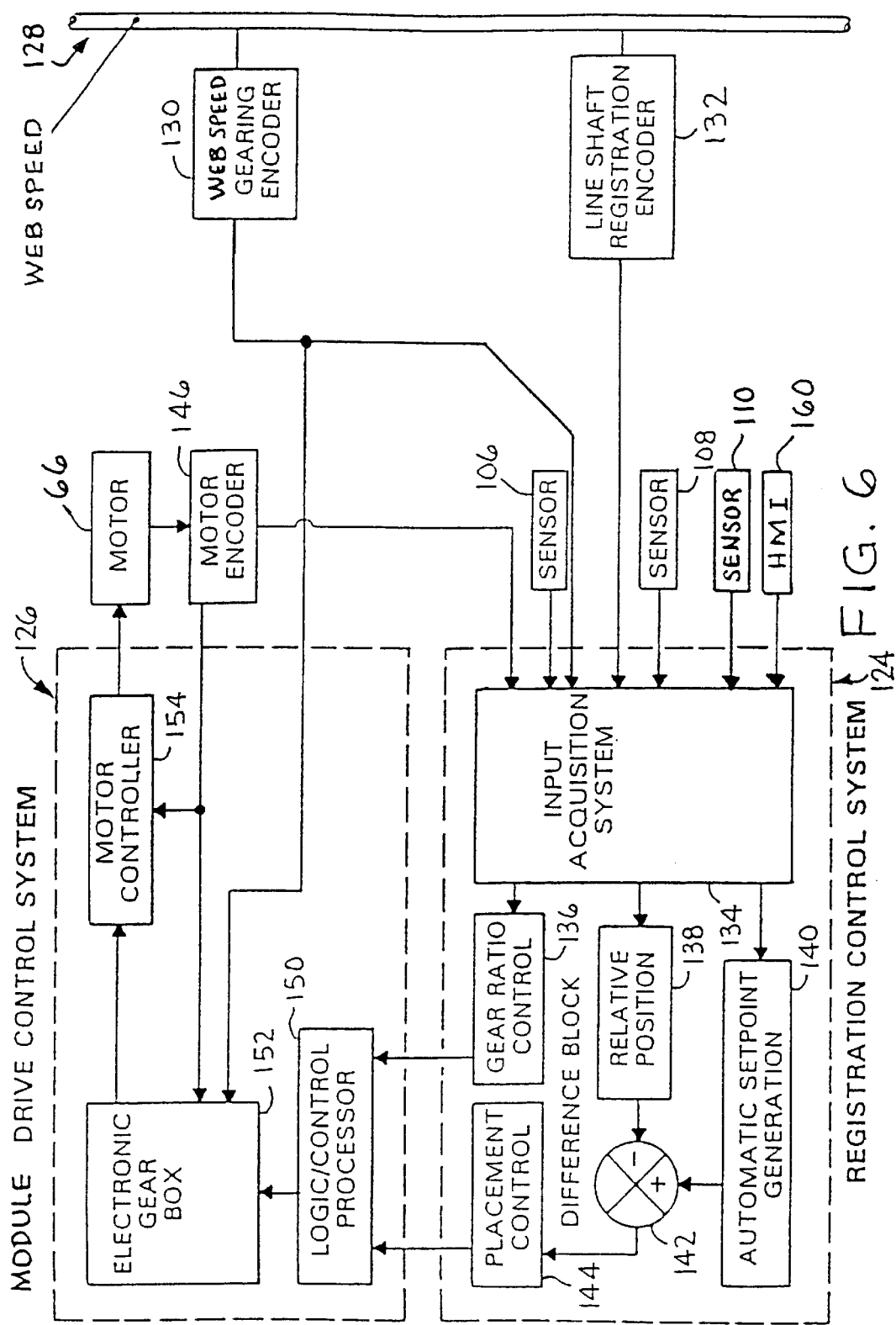
FIG. 6 illustrates a schematic block diagram of the flow of data utilized in conjunction with the apparatus and process in FIGS. 5A and 5B.

The separating device 48 (FIG. 5A) is driven by a motor 66 (FIG. 6). The knife roll 56 and anvil roll 58, conveyor assemblies 50, debulker assembly 49, wrap sheet folder assembly 51, pad transfer conveyor 62, and fluff forming drum 47 are desirably all operatively coupled, electrically and/or mechanically, to the motor 66. Motor 66 is controlled through a registration control system 124 (FIG. 6) and a module drive control system 126 (FIG. 6) to register the absorbent pads 32 with respect to the first layer 80.

A typical module drive system includes a module drive control system 126 (FIG. 6) for controlling the motor 66, and can be any suitable system such as those described in the U.S. patents incorporated by reference herein. It is important that a module drive system for any of the various modules (FIG. 6) is one that is capable of performing two types of speed variations which will be described in greater detail hereafter. One speed variation is to increase a present speed of rotation to a faster speed of rotation, or to decrease a present speed of rotation to a slower speed of rotation. The other speed variation is a momentary speed variation comprising an incremental advance phase move, which is a momentary speed increase of the component module to provide a measured decrease in the component repeat length, or an incremental retard phase move, which is a momentary speed decrease of the component module to provide a measured increase in the component repeat length.

The term "momentary speed increase" refers to increasing a first speed to a higher second speed for a selected period of time, and then allowing the speed to return to the first speed, in order to advance the position of the component by a measured amount. The term "momentary speed decrease" refers to decreasing a first speed to a lower second speed for a selected period of time, and then allowing the speed to return to the first speed, in order to retard the position of the component by a measured amount.

The present invention can be utilized to register one or more components to a a reference mark on the first layer so that the components are located in the desired position in an individual product. In this particular description, a component, such as the absorbent pad 32, is brought in registration with a reference mark 74 (FIGS. 3, 5A and 5B) on first layer 80. The relative location of the absorbent pad 32 on first layer 80 is measured in encoder counts, from a primary lineshaft registration encoder 132 (FIG. 6), between a reference mark 74 (FIG. 5A) as detected by a sensor 110, and its corresponding absorbent pad 32 as detected by a sensor 108. This measurement is used to controllably register an absorbent pad 32 to its corresponding reference mark 74, thereby placing absorbent pad 32 in the desired position in a training pant. The reference marks 74 need not be visible to the human eye on the product, but must be able to be sensed or detected mechanically, electrically, or the like. It should be noted that the reference marks 74 in FIGS. 5A and 5B are shown as raised objects relative to the first layer 80 solely for purposes of explanation.

With reference to FIG. 3, there is illustrated a portion of continuously moving layer 80 having a plurality of graphics 38 and reference marks 74 preprinted or pre-positioned thereon. Associated with each graphic 38 is a printed waistband 76. Each reference mark 74 also can be used to properly position an absorbent pad 32 (FIG. 4) with an associated graphic 38. The reference marks 74 are positioned off or separated from graphics 38, but could be printed directly on the graphics 38 so as to be within the design of the graphics. Furthermore, the reference marks 74 can be eliminated, and a portion of a graphic 38 can be used as a reference mark for selectively positioning a corresponding absorbent pad or other component. For purposes of explanation and manufacture, however, reference marks 74 are provided a selected distance apart from respective graphics 38.

Returning now to FIG. 5A, a suitable adhesive is applied to a surface of the first layer 80 by an adhesive applicator 98 to laminate absorbent pad 32 to the first layer 80. The adhesive applicator 98, as well as the adhesive applied thereby, can be any type of applicator suitable for the desired adhesive pattern, and appropriate and compatible for the materials to be joined. A first sensing device, such as a sensor 106, is suitably positioned desirably between the separating device 48 and the mating roll 64 for detecting or sensing each absorbent pad 32 and generating a signal in response thereto. A-suitable sensor 106 is a Banner RSBF scanner block, RPBT wiring base, IR 2.53S fiber-optic pair device, available from Banner Engineering Corp., of Minneapolis, Minn.

Second and a third sensing devices, such as the photoeye 108 and the sensor 110, are positioned downstream of the mating roll 64. The term "downstream" refers to a position in the training pant manufacturing process that is closer to completion of the final product relative to another position. The photoeye 108 can be the same type as described above in relation to sensor 106. Sensor 110 is desirably a SICK detector model LUT 3-6 available from SICK OPTIK ELEKTRONIK, Inc., having a business office in St. Paul, Minn. Sensor 110 is designed to detect or sense a reference mark 74 and generate a signal in response thereto. In this particular description, both sensors 106 and 108 optically detect or sense a product component, such as absorbent pad 32, and generate a respective signal in response thereto. If desired, photoeyes 106 and 108 can sense other components, such as waist elastics, leg elastics, fastening tapes utilized in diapers, or the like.

Figures 9, 10:
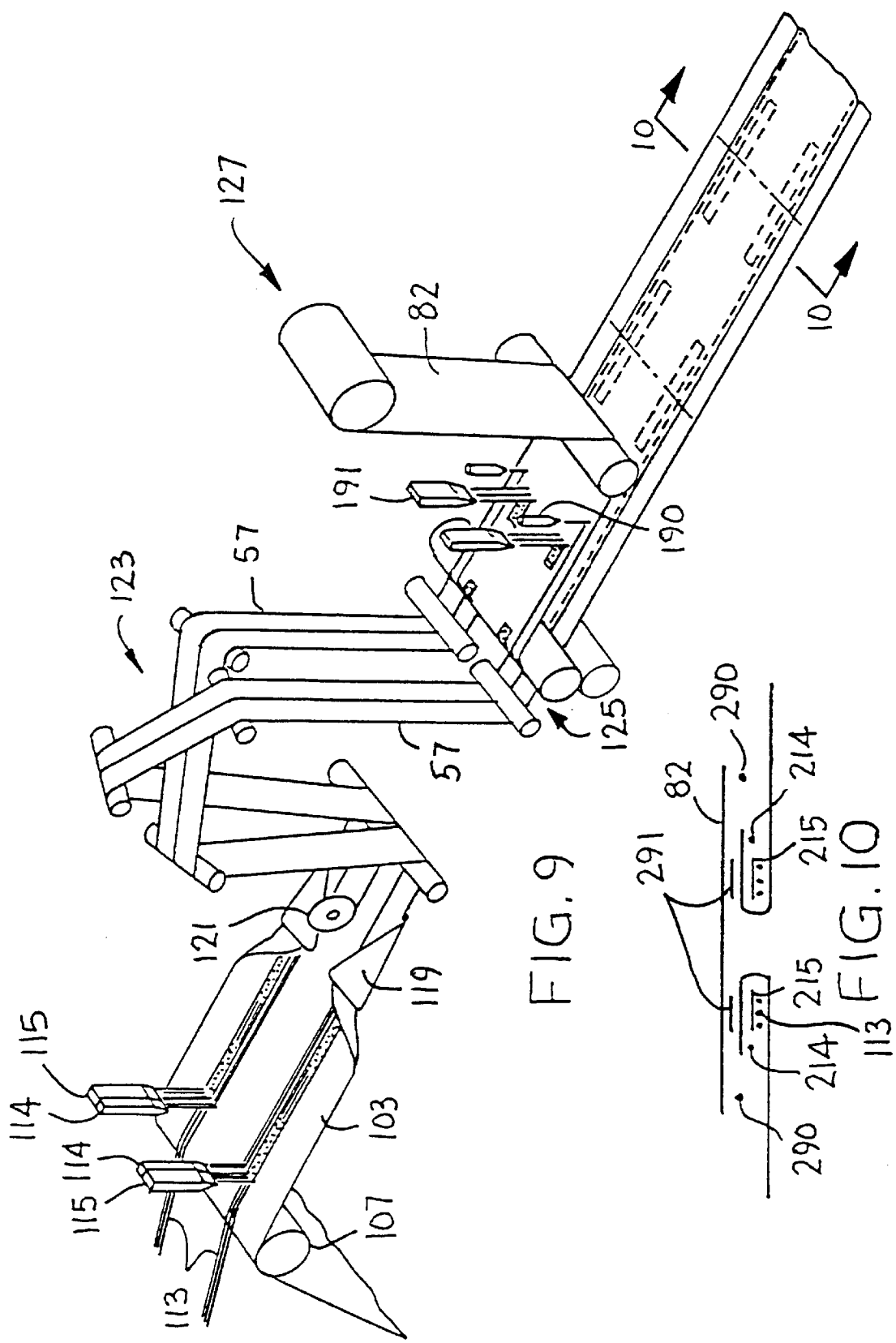
FIG. 9 graphically illustrates one embodiment of a portion of the process shown in FIG. 5B, for assembling a liner-flap composite structure.
FIG. 10 illustrates a cross sectional representation of the components of the liner-flap composite structure as assembled in FIG. 9.

With reference to FIGS. 5B and 9, a layer of containment flap material 103 is supplied from a flap material supply device 105 and moves toward laminating roll 107. The flap material supply device 105 can be any standard unwind mechanism that generally comprises a pair of spindles, a festoon assembly, and a dancer roll for providing the flap layer 103 at a desired speed and tension. One example of a standard unwind is a model MB 820, available from Martin Automatic Corporation of Rockford, Ill.

Another supply device 109 desirably provides spaced apart and continuous elastic members 113 in a selected prestretched condition. One suitable supply device 109 for providing the prestretched elastic members 113 is an unwind model T6M-8 available from Accratec Engineering, Inc., of Neenah, Wis. This particular unwind controllably adjusts the speed of the elastic members 113 in order to provide them with a selected tension or elongation, which ultimately will provide the desired elasticity to a liner-flap composite structure 55 (FIGS. 4 and 5B). The elastic members 113 are surface driven by the supply device 109, in that a motor driven drive roll in the unwind provides the elastic members 113 at a desired speed. By controllably adjusting the speed of the elastic members 113, the elongation of the elastic members 113 can be controlled, thereby controlling the tension of the elastic members 113.

An adhesive applicator 115 selectively applies adhesive intermittently in the correct position and desired length in reference to the signal generated by a sensor 110 to join the elastic members 113 to the flap layer 103 in the desired location. The adhesive applicator 115, as well as the adhesive applied thereby, can be any type suitable for the desired adhesive pattern, and which are appropriate and compatible for the materials to be joined. After reference mark 74 is detected, the registration control system 124 waits a predetermined number of encoder counts from lineshaft registration encoder 132, and turns on adhesive applicator 115. The adhesive applicator 115 remains on for a predetermined number of encoder counts, whereupon it is turned off by registration control system 124, all in accordance with preprogrammed instructions.

A second adhesive applicator 114 continuously applies an adhesive pattern to flap layer 103 to hold a fold formed by folder 119 on both side edges of flap layer 103 to cover the flap elastics 113 as illustrated in FIG. 9. If desired, a single adhesive applicator can be used to apply both the intermittent and continuous adhesive patterns, rather than using multiple applicators. The intermittent adhesive pattern 215 from applicator 115 and a continuous adhesive pattern 214 from applicator 114 are shown in FIG. 10.

The containment flap material 103 proceeds through slitter 121 (FIGS. 5B and 9) and CD spacing guides 123. The slit flap composite layer produces two flap composites 57. The CD spacing guides 123 reverse the position of the two flap composites 57 to change the location of the elastic 113 from an outer position to an inner position. The flap composites 57 are attached to topsheet layer 82 with adhesive at nip assembly 125. Layer 82, which will subsequently become liner or topsheet 36 (FIG. 1), moves from liner supply device 127 to adhesive applicators 190 and 191, which apply adhesive continuously and intermittently for attaching layer 82 to the flap composite layer. Two continuous adhesive beads 290 from applicator 190 attach the side edges of the layer 82 to the flap composites 57 in the desired location as illustrated in FIG. 10. Two intermittent adhesive patterns 291 from application 191 attach the ends of the flap composite to the layer 82 to maintain their desired cross-machine directional location for both manufacturing purposes and product performance. The adhesive pattern is positioned at the desired location and desired length with reference to a signal generated by sensor 110. The above steps form liner-flap composite structure 55 (FIG. 5B).

Adhesive is applied to the liner-flap composite structure 55 by adhesive applicator 97 (FIG. 5B). Layer 55 is then superimposed over continuously moving layer 80, and together the layers 80, 55 pass through a product tacker 100 comprising a roll 102, which is driven by web speed lineshaft 128 (FIG. 6), and a rubber-coated idler roll 104. The tacker 100 compresses the layers 80, 55 together cause the applied adhesive to join them together, thereby forming a continuously moving composite 93 (FIGS. 4 and 5B).

The adhesive applicators disclosed herein may be any type suitable for the corresponding application, as are commonly known and used in the art. For example, suitable applicators are available from Nordson Corporation, Norcross, Ga.

With reference to FIG. 4, there is illustrated a continuously moving composite layer 93 comprising layers 80, 55 having absorbent pads 32 therebetween. Each printed waistband 76 can be cut along a respective cut line 120 in order to form individual products. In FIG. 4, once cut lines 120 have been separated, a front waist edge 116 and a back waist edge 118 are formed for each assembled product.

One of the important features of the present invention as illustrated in FIGS. 3 and 4 is the position or placement of each product component relative to the reference mark 74. Other marks or product components can be held in constant phase relationship to the reference mark 74 using their corresponding reference marks, which will result in these product components being placed in their desired position in each product. For example, absorbent pad 32 (FIG. 4) can be placed in the desired location in the product and elastic members 113 (FIG. 9) can be attached in the desired location in the product by controlling these attributes in constant phase relationship to the reference mark 74 during the process. As previously stated, although this description of registering components is made with reference to the reference marks 74, a component, or components, may serve as a reference for other components.

Referring to FIG. 6, there is schematically illustrated a control system of the present invention comprising a registration control system 124 that receives various generated signals, processes them in accordance with preprogrammed instructions, and generates output signals to a module drive control system 126. The module drive control system 126 receives the signals from the registration control system 124, and in response thereto operatively adjusts the drive motor 66. A web speed lineshaft 128 directly drives various mechanisms or indirectly drives, through a system of gears and other coupling devices, both electrical and mechanical, other mechanisms or modules. Lineshaft 128 is driven at a selected constant speed, by any suitable means well known in the art. Thus, those mechanisms driven by lineshaft 128 can be driven at a corresponding constant speed, which may or may not be the same speed as that of lineshaft 128. A web speed gearing encoder 130 and a lineshaft registration encoder 132 are operatively coupled to lineshaft 128. Examples of such encoders include an H25D-SS-2500-ABZC-8830-LED-SM18 (which can be used as encoder 130), available from BEI Motor System, Co. of Carlsbad, Calif., and a 63-P-MEF-1000-T-0-00 (which can be encoder 132) available from Dynapar Corp. of Gurnee, Ill.

The registration control system 124 comprises hardware and/or preprogrammed software instructions, and can be represented, with reference to FIG. 6, as comprising an input acquisition system 134, a gear ratio control 136, a relative position block 138, an automatic setpoint generator 140, a difference block 142, and a placement control 144. Additionally, the registration control system 124 may also comprise the components shown in FIG. 11, including a software resetable counter 234, a comparator 236 and a calibrator 238, which are adapted to control the adhesive solenoid registration function, as further described hereinafter. The registration control system 124 includes a computer, which can comprise, for example, a VME-based microprocessor, such as a SYS68K/CPU-40B/4-01 available from Force Computers, Inc. of Campbell, Calif.

Figure 11:
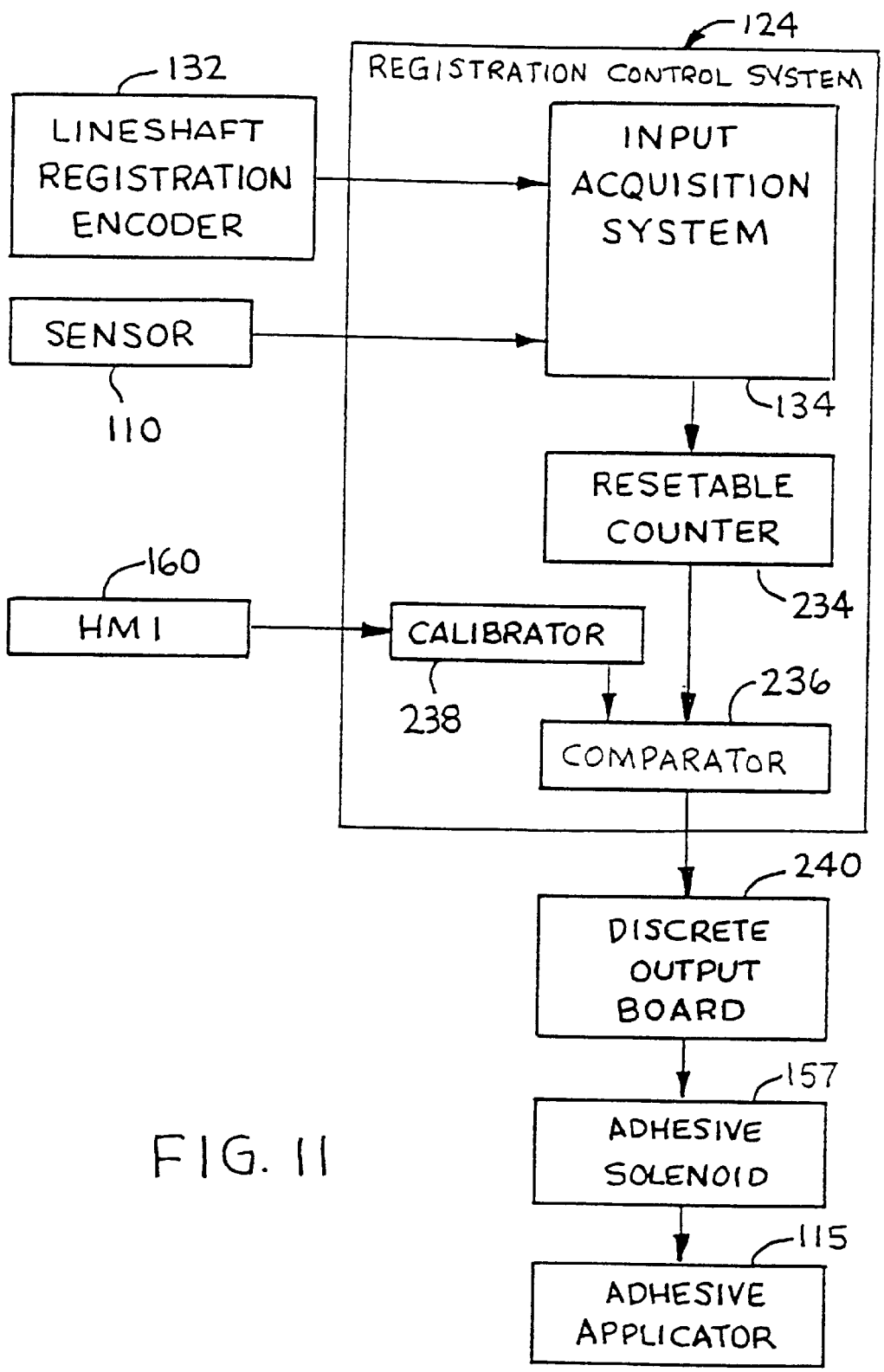
FIG. 11 illustrates a schematic block diagram of the control used for pulsed adhesive application in FIG. 9.

As illustrated in FIGS. 6 and 11, input acquisition system 134 receives the following generated signals: (i) a signal from a motor encoder 146 operatively coupled to the drive motor 66, (ii) a signal from sensor 108 (FIG. 5A), (iii) a primary marker signal from lineshaft registration encoder 132, (iv) a pulsetrain signal from lineshaft registration encoder 132, (v) a signal from sensor 110, (vi) a signal from sensor 106, (vii) a pulsetrain signal from web speed gearing encoder 130, and (viii) a human-machine interface 160.

Input acquisition system 134 receives and counts the pulses generated by motor encoder 146, web speed gearing encoder 130, and lineshaft registration encoder 132, and receives signals from sensors 106, 108 and 110. Between signals generated by sensor 110, the input acquisition system 134 accumulates counts from motor encoder 146, web speed gearing encoder 130, and lineshaft registration encoder 132, and the input acquisition system 134 performs preprogrammed instructions that are specific to the respective received signals, and stores the results of the instructions.

The input acquisition system 134 performs the following functions for the gear ratio control 136. The input acquisition system 134 counts the pulses received from lineshaft registration encoder 132, and receives signals generated by sensor 106 and sensor 110. The input acquisition system 134 then measures the counted pulses from lineshaft registration encoder 132, representing a distance between every two successive reference marks 74 as sensed by sensor 110, and performs a running average of those measured counts. This is the machine reference signal running average. The term "running average" refers to averaging the same number of data; for example, for each newly received datum input, the oldest datum is removed from the averaging calculation. Input acquisition system 134 also measures the counted pulses from lineshaft registration encoder 132 representing a distance between every two successive absorbent pads 32 as sensed by sensor 106, and performs a running average of counts between signals from sensor 106. This is the absorbent pad signal running average.

The machine reference signal running average and the absorbent pad signal running average are used to derive the gear ratio for gear ratio control 136. This averaging "smoothes out" the measurements due to the variability of the apparatus, process and raw materials. The number of measurements to average is controllable, and is set or determined by providing an appropriate instruction, via manual input, in any suitable manner well known in the art, such as through the human-machine interface 160. In conjunction with performing a running average of the measured counts, the input acquisition system 134 performs a filtering function, which is preprogrammed, to filter out signal anomalies. Examples of such signal anomalies include a dirty sensor, missing or extra reference marks 74, movement or weaving of the layers, measuring the counts outside a preprogrammed range for averaging purposes, known inaccurate data due to registration control events, or the like.

For the relative position block 138, the input acquisition system 134 counts the pulses received from lineshaft registration encoder 132, and receives signals generated by sensor 106 and sensor 110. Relative position block 138 counts the pulses between receiving a signal from sensor 110 and receiving a signal from sensor 106, and performs a running average of these counts. This running average is called the absorbent pad relative position. The relative position block 138 then generates and transmits a relative position value to the difference block 142.

After the absorbent pads 32 are placed on layer 80, the placement is checked using sensors 108 and 110. By this inspection, the actual position of the absorbent pad 32 relative to the corresponding reference mark 74 is determined. If the actual position is not the desired position, the setpoint of the placement control is automatically corrected. This automatic correction is performed by the automatic setpoint generator 140. To perform this function, the input acquisition system 134 counts the pulses received from lineshaft registration encoder 132, and receives the signals generated by sensor 108 and sensor 110. The input acquisition system 134 counts the pulses between receiving a signal from sensor 110 and receiving a signal from sensor 108, and transmits the count value to the automatic setpoint generator 140 which calculates a running average and standard deviation of these count values. This running average is called the absorbent pad automatic setpoint position, and this calculation results in the actual position value. With this calculated running average, the automatic setpoint generator 140 determines the setpoint for placement control 144 in accordance with preprogrammed instructions.

The automatic setpoint generator 140 then compares the standard deviation of the count values with a preset limit, which has been manually entered through a human machine interface (HMI) 160. If the standard deviation is outside the preset limit, the automatic setpoint generator 140 will ignore that datum and not determine a new setpoint. In this case, the standard deviation data is considered too variable to make an accurate setpoint adjustment. If the standard deviation is within the preset limit, the automatic setpoint generator 140 will determine the difference between the actual position value and a manually entered target value, which is the desired actual position value. If the new calculated difference is determined, by automatic setpoint generator 140, to be within a prescribed range, no further action or calculation will be made. However, if the difference is outside the prescribed range, the automatic setpoint generator 140 will determine a new control setpoint. This new control setpoint is derived by adding to the current setpoint the difference between the target value and actual position value.

The various calculations and functions performed by the input acquisition system 134 are utilized by other portions of the registration control system 124 in order to generate commands to the module drive control system 126 (FIG. 6). The module drive control system 126 generally comprises a logic/control processor 150, an electronic gear box 152, and a motor controller 154. The module drive control system 126 can comprise, for example, a Reliance Distributed Control System made by Reliance Electric, Co., including a Reliance Electric Automax Processor and associated hardware. In one particular embodiment, the electronic gear box 152 (FIGS. 6–7) comprises a dual-axis card that is part of the Reliance Distributed Control System unit and is used to control the position of motor 66.

Within the registration control system 124, the gear ratio control 136 queries the input acquisition system 134 every 20 products, i.e., every 20 machine product repeat lengths, for the absorbent pad signal running average, as previously defined. The number of product lengths determining a query from gear ratio control 136 is adjustable, and can be changed manually by the operator.

In the described embodiment, the absorbent pad signal running average is the module repeat value. The module repeat value is used by gear ratio control 136 to perform a gear ratio calculation in accordance with preprogrammed instructions, thereby determining a new gear ratio value. That new gear ratio value is then transmitted to the logic/control processor 150 of module drive control system 126. The gear ratio value is calculated by dividing the module repeat value, obtained from sensor 106, by the machine reference signal running average, obtained from sensor 110. The advantage of this is the ability to controllably regulate the repeat of absorbent pads 32, without comparing to a target value, and the ability to rapidly compensate for processing irregularities and changes of the material that can alter the desired repeat of the absorbent pads 32 as the reference marks 74 vary.

Once every machine product repeat length, the difference block 142 (FIG. 6) determines the difference between the current setpoint from automatic setpoint generator 140 and the associated relative position value from relative position block 138, which is the placement error. The difference block 142 transmits this placement error, in counts of lineshaft registration encoder 132, to the placement control 144. The placement control 144 compares the placement error to a tolerance band 170 (FIG. 8), which defines an acceptable deviation of the relative position value about the current setpoint. The tolerance band 170 remains constant about the setpoint, but the setpoint can vary as calculated by automatic setpoint generator 140. As a result, while the position control of the absorbent pad is accomplished by drive motor 66, the setpoint for this position control is accurately derived from the signals generated by sensor 108 and sensor 110.

Figure 8:
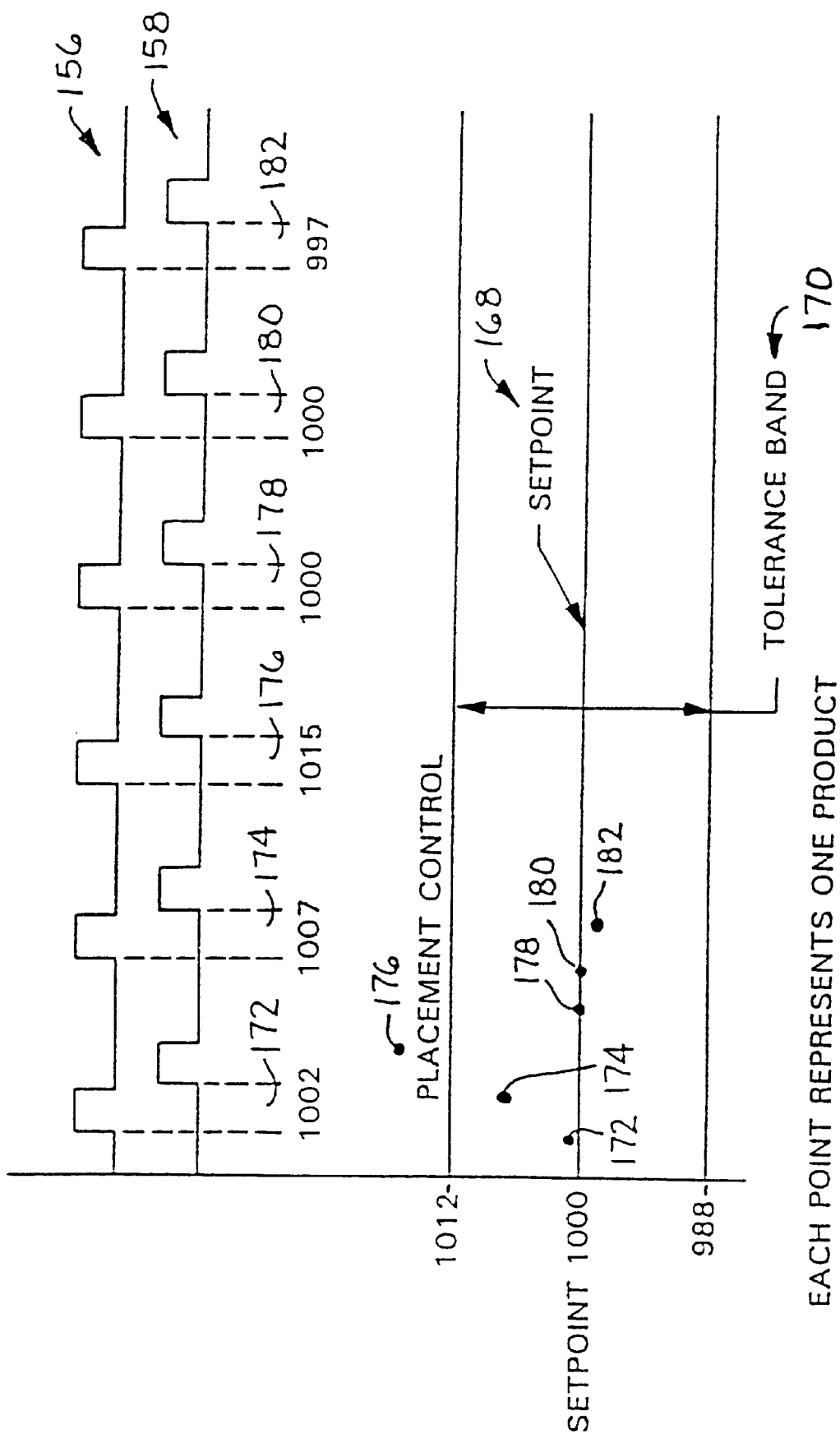
FIG. 8 graphically illustrates a placement control utilized in conjunction with the apparatus and process in FIGS. 5A and 5B.

With reference to FIG. 8, there is illustrated one derived setpoint 168 having a prescribed tolerance band 170. For purposes of explanation, the control setpoint 168 has a value of 1,000 counts, and the tolerance band 170 represents a deviation of plus or minus 12 counts. Each of the datum points 172, 174, 176, 178, 180 and 182, represents one product's relative position value as calculated by relative position block 138. Waveform 156 represents signals generated by sensor 110, and waveform 158 represents signals generated by sensor 106. If a placement error value remains within tolerance band 170, no placement command will be generated. However, if a placement error value is outside tolerance band 170, as illustrated by datum point 176, then placement control 144 will generate a placement command. The placement command is directly proportional to the size of the difference represented by the value from difference block 142 and calls for a measured advance or retard in the position of absorbent pad 32. The generated placement command is then transmitted to the logic/control processor 150 of the module drive control system 126.

FIG. 8 illustrates an example of how placement control 144 (FIG. 6) compares each datum point to a current control setpoint in order to generate a placement error. The placement error for each datum point is compared to tolerance band 170 to determine if a placement command should be generated. In the example, point 176 is the only datum point where the placement error falls outside the tolerance band 170, which causes a placement command to be generated, thereby causing a following datum point to fall within the tolerance band 170. For ease of understanding, FIG. 8 uses single datum points rather than running averages.

Figure 7:
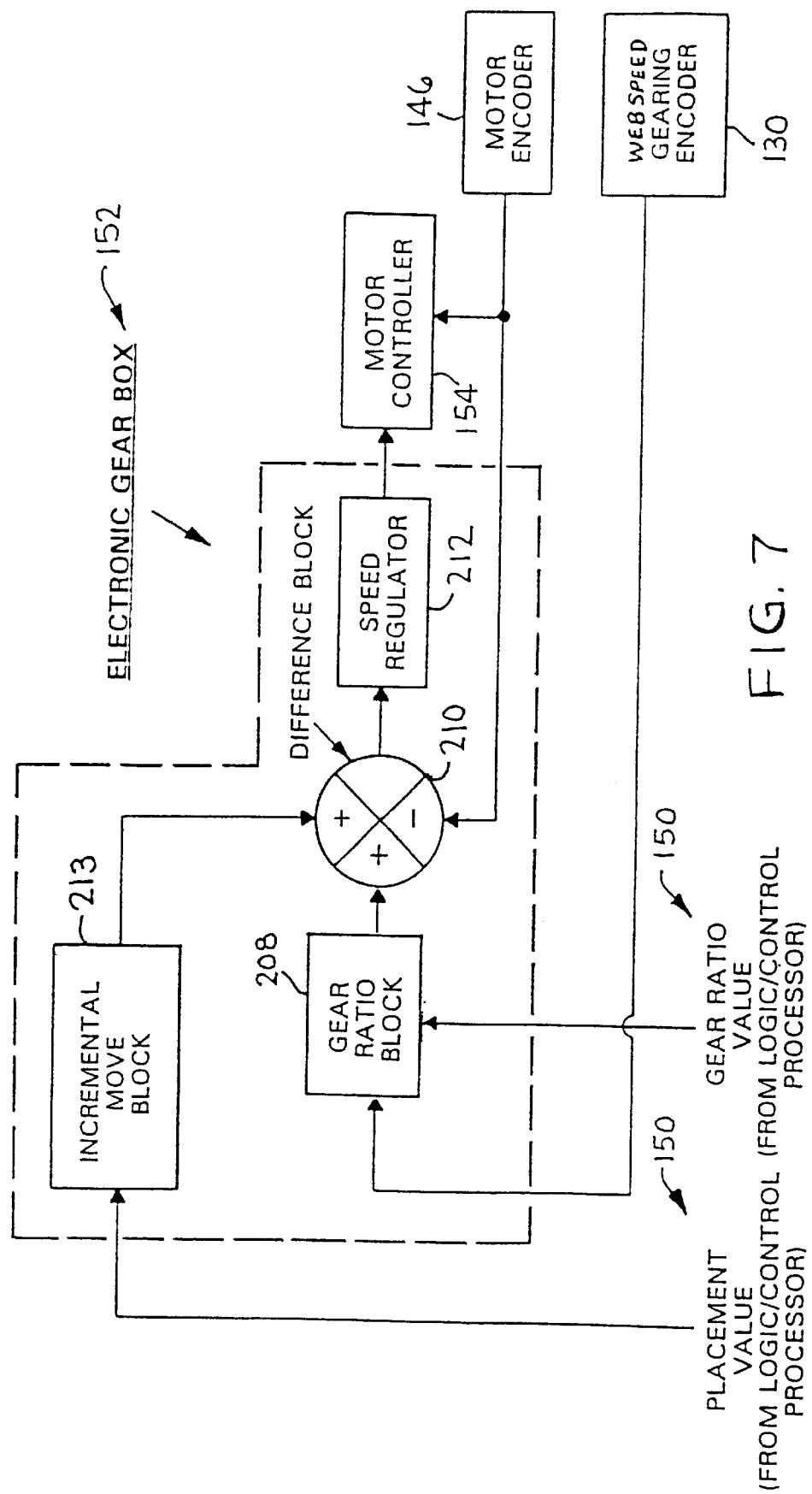
FIG. 7 illustrates a block diagram of an electronic gear box shown in FIG. 6.

The logic/control processor 150 (FIGS. 6 and 7) searches for and receives new values from the registration control system 124. Specifically, processor 150 searches for and receives gear ratio values from gear ratio control 136, and placement values from placement control 144. For each updated gear ratio value, processor 150 transmits a command in accordance with preprogrammed instructions to the electronic gear box 152 to modify the value used in a gear ratio block 208 (FIG. 7). For each updated placement value received from placement control 144, processor 150 transmits a placement command in accordance with preprogrammed instructions to electronic gear box 152 to modify the value used in incremental move block 213 (FIG. 7).

Referring to FIG. 7, electronic gear box 152 is schematically illustrated as comprising a gear ratio block 208, a difference block 210, a speed regulator 212, and an incremental move block 213. The gear ratio block 208 receives a gear ratio value from logic/control processor 150 (FIG. 6), and receives a pulse train from the web speed gearing encoder 130. Gear ratio block 208 scales the pulse train from gearing encoder 130 and applies the gear ratio value to it in order to generate a reference signal to difference block 210. Difference block 210 receives the reference signal from gear ratio block 208, and also receives a feed back signal from motor encoder 146, which communicates the current speed of the motor 66. The difference block 210 determines the difference between the signals and generates a command signal to the speed regulator 212, which generates a speed reference signal to the motor controller 154. Thus, the electronic gear box 152 precisely links the speed of the drive motor 66 to the machine reference signal running average through an electronically changeable gear ratio. This effectively synchronizes the feed rate of the absorbent pads 32, governed by the speed of the motor 66, to the feed rate of the reference marks 74 on layer 80.

With reference to FIGS. 6 and 7, electronic gear box 152 also receives a placement value from logic/control processor 150. The placement value is received by incremental move block 213, which is part of electronic gear box 152. Incremental move block 213 performs a "one time" move to appropriately adjust the reference signal by a measured amount of drive motor encoder 146 counts, thereby calculating an exact one time increase or decrease in the feed rate of the absorbent pad 32 being supplied by drive motor 66. This can be done by relating the number of encoder counts of the motor encoder 146 to an actual feed rate of the absorbent pads 32 supplied by the separating device 48 (FIG. 5A). In response to the placement command, an incremental move signal is generated and temporarily added to the difference block 210, which increments or decrements the reference signal received from the gear ratio block 208, thereby resulting in a momentary change in the speed command signal sent to the speed regulator 212. Motor controller 154 receives the speed command signal from electronic gear box 152 (FIG. 6) and varies the speed of the motor 66.

The desired registration of absorbent pads 32 to a machine reference signal sensed by sensor 110 can be accomplished as described above. By selectively controlling the distance between successive absorbent pads 32 (FIG. 5A), each absorbent pad 32 can be desirably registered with an associated machine reference signal sensed by sensor 110. Controlling the spacing and placement of the absorbent pads 32 relative to the reference marks 74 accommodates or corrects for variations or other types of anomalies that may be present in the materials, apparatus or process.

A control system for the adhesive applications to construct and apply the liner-flap composite structure 55 (FIGS. 5B, 9) is schematically illustrated in FIG. 11. In the registration control system 124, a software resetable counter 234 counts lineshaft registration encoder 132 pulses and resets to zero when it reaches the machine reference signal running average. Adhesive applicator 115 is turned on and off at predetermined operator selectable counts of the software resetable counter 234. The adhesive applicator 115 remains on for the length that the elastic is to be attached. The counts from registration encoder 132 are directly related to the distance between reference marks 74. For example, the gearing on the machine can be arranged such that a machine reference signal running average of 2000 counts corresponds to 500 millimeters between reference marks 74, yielding 4 counts per millimeter for easy operator input of component placement adjustments. The machine reference signal running average, as described above, is determined by the input acquisition system 134 and represents a distance between every two successive reference marks 74 as detected by sensor 110.

The input acquisition system 134 relays the pulse train from the lineshaft registration encoder 132 and the machine reference signal running average to the resetable counter 234 to provide a position indication within each product as it passes the adhesive applicator 115. Operator selectable setpoints are received from the human machine interface 160 and converted from millimeters to counts equivalent to the lineshaft registration encoder counts in calibrator 238. The value from the resetable counter 234 is compared in accordance with preprogrammed instructions in a comparator 236 to the operator selectable setpoints. The comparator 236 generates a signal which determines when the adhesive applicator should be turned on and off. The signal from the comparator 236 is sent to a discrete output board 240 which controls the adhesive solenoid 157 which in turn operates the adhesive applicator 115.

In one particular embodiment, for instance, the flap elastic attachment adhesive is desirably placed between 100 and 400 millimeters from the beginning of the product, as measured from the location of the reference mark 74. The operator inputs the selectable setpoints of 100 millimeters representing the starting point for adhesive application and 300 millimeters representing the duration of adhesive application. The calibrator 238 converts these setpoints to encoder counts of 400 and 1200, using the above-referenced example where the gearing on the machine yields 4 counts per millimeter of layer 80 in the machine. The calibrator 238 sends the converted setpoints to the comparator 236 where it is stored and used until a new setpoint is entered. Where, for example, the machine reference signal running average is 2030, the resetable counter 234 counts from 0 to 2030 for each product. Whenever the resetable counter reaches 400 counts, the comparator equates this value with the setpoint in counts and sends a signal to the discrete output board 240 which in turn energizes the adhesive solenoid 157, thereby starting the flow of adhesive from the adhesive applicator 115. The adhesive solenoid 157 remains energized until the resetable counter reaches 1200 counts, whereupon the comparator equates this value with the setpoint in counts and turns off the signal. When the resetable counter 234 reaches 2030 counts, it resets to zero.

The input acquisition system 134 similarly controls adhesive applicator 191 (FIGS. 5B, 9) to attach the ends of the flap composite 57 to layer 82 to provide the desired machine directional attachment for both manufacturing purposes and product performance.

Normally, the machine determines the product repeat length. In order to change from one product length to another, a different set of length-specific grade parts is required. In this invention, the reference material determines the product repeat length. To accomplish this, the invention provides a process for adjusting the speed of module drive motors, so that the placement of product components can be appropriately registered using the machine reference signal sensed by sensor 110. Subsequently, this control method can also be used to control the placement of other intermittent processes, including without limitation adhesive application, printing, curving, contouring, cutting, or the like, and in the process, thereby achieving relative placement of product components. This invention therefore enables quick grade change capability by changing layer 80 and having the placement of all subsequent components follow the position of the registration marks 74 contained thereon.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A process for registering a plurality of discrete components of a continuously moving second layer to reference marks on a continuously moving first layer comprising the steps of:

providing a continuously moving first layer including a plurality of reference marks selectively positioned thereon;

sensing a distance between two successive reference marks on the first layer and generating a signal in response to the sensed distance;

providing a second layer having a plurality of continuously moving discrete components;

sensing a distance between two successive components of the second layer and generating a signal in response to the sensed distance;

synchronizing a feed rate of the components of the second layer to a feed rate of the reference marks on the first layer;

aligning the components of the second layer a set distance to correspond with the reference marks on the first layer;

superimposing the discrete components of the second layer onto the continuously moving first layer;

providing a continuously moving third layer formed from a plurality of continuously moving individual components;

applying a first adhesive intermittently to at least one continuously moving individual component of the continuously moving third layer by detecting a reference mark on the continuously moving first layer and, in response, turning on the adhesive applicator at a set time for a set duration;

superimposing the continuously moving third layer onto the continuously moving first layer subsequent to superimposing the discrete components of the second layer onto the continuously first layer; and joining the at least one continuously moving individual component of the continuously moving third layer to at least one other continuously moving individual component.

2. An apparatus for registering a plurality of discrete components of a continuously moving second layer to reference marks on a continuously moving first layer, comprising:

a device for providing a continuously moving first layer including a plurality of reference marks selectively positioned thereon;

a device for conveying a second layer having a plurality of discrete components toward the continuously moving first layer;

a sensor for sensing each of the reference marks on the first layer, and a device for generating a reference mark signal in response thereto;

a device for measuring the distance between two successive reference mark signals;

a sensor for sensing each of the components of the second layer, and a device for generating a component signal in response thereto;

a device for measuring the distance between two successive component signals;

a device for generating a corrective control signal;

a device for adjusting a feed rate of the discrete components of the second layer in response to the corrective control signal;

a device for superimposing the discrete components of the second layer onto the continuously moving first layer;

an apparatus for forming a continuously moving third layer from a plurality of continuously moving individual components including at least one applicator for applying adhesive intermittently to at least one of the continuously moving individual components;

a sensor that detects a reference mark on the continuously moving first layer and, in response turns on the at least one adhesive applicator at a set time for a set duration;

a device for superimposing the continuously moving third layer onto the first continuously moving layer subsequent to superimposing the discrete components of the second layer onto the continuously moving first layer; and a device for compressing the first, second and third continuously moving layers.

* * * * *